(12) United States Patent
Koike

(10) Patent No.: US 10,646,181 B2
(45) Date of Patent: May 12, 2020

(54) BREAST TYPE IDENTIFICATION DEVICE, METHOD, AND PROGRAM

(71) Applicant: FUJIFILM CORPORATION, Minato-ku, Tokyo (JP)

(72) Inventor: Takafumi Koike, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 66 days.

(21) Appl. No.: 16/109,762

(22) Filed: Aug. 23, 2018

(65) Prior Publication Data

US 2019/0090833 A1 Mar. 28, 2019

(30) Foreign Application Priority Data

Sep. 28, 2017 (JP) ................. 2017-187878

(51) Int. Cl.
*A61B 6/00* (2006.01)
*G06T 7/13* (2017.01)
*G06T 7/00* (2017.01)
*G06K 9/00* (2006.01)
*A61B 6/02* (2006.01)

(52) U.S. Cl.
CPC ............. *A61B 6/502* (2013.01); *A61B 6/025* (2013.01); *A61B 6/463* (2013.01); *A61B 6/5217* (2013.01); *G06K 9/00* (2013.01); *G06T 7/0012* (2013.01); *G06T 7/13* (2017.01); *G06T 2207/10116* (2013.01); *G06T 2207/20081* (2013.01);
(Continued)

(58) Field of Classification Search
None
See application file for complete search history.

(56) References Cited

U.S. PATENT DOCUMENTS 8,160,346 B2 * 4/2012 Gatesoupe .............. G06T 7/155
378/4
9,788,806 B2 * 10/2017 Hamauzu ............... A61B 6/502
(Continued)

FOREIGN PATENT DOCUMENTS

| JP | 2005021456 | * | 1/2005 |
| JP | 2005-065857 A | | 3/2005 |
| JP | 2006-263055 A | | 10/2006 |

OTHER PUBLICATIONS

A New CAD System for Breast Microcalcifications Diagnosis H. Boulehmi, H. Mahersia and K. Hamrouni National Engineering School of Tunis, LR-SITI ElManar University, BP-37, Le Belvédère; 2016.*

*Primary Examiner* — Nancy Bitar
(74) *Attorney, Agent, or Firm* — SOLARIS Intellectual Property Group, PLLC

(57) ABSTRACT

A first detection unit detects a breast region and a skin line from a breast image, and a first index value calculation unit calculates a first index value indicating the single composition degree of the breast region. A second detection unit detects a boundary between the adipose tissue and the mammary gland tissue in a predetermined range from the skin line toward the inside of the breast region in the breast image. A second index value acquisition unit acquires a second index value indicating the degree of clogging of mammary glands with respect to the breast region based on at least one of the strength of the boundary or the distance from the skin line. An identification unit identifies the type of the breast based on the first and second index values.

8 Claims, 12 Drawing Sheets

(52) U.S. Cl.
CPC ............... *G06T 2207/20168* (2013.01); *G06T 2207/30068* (2013.01)

(56) References Cited

U.S. PATENT DOCUMENTS

| | | | |
|---|---|---|---|
| 10,098,600 B2* | 10/2018 | Ning | A61B 6/032 |
| 10,169,867 B2* | 1/2019 | Fieselnnann | G06T 7/0012 |
| 2006/0274145 A1* | 12/2006 | Reiner | G06F 19/321 |
| | | | 348/62 |
| 2007/0248210 A1* | 10/2007 | Selse | A61B 6/0414 |
| | | | 378/37 |
| 2010/0246924 A1* | 9/2010 | Morita | A61B 5/4872 |
| | | | 382/132 |
| 2011/0229006 A1* | 9/2011 | Morita | G06T 7/0012 |
| | | | 382/132 |
| 2013/0223711 A1* | 8/2013 | Knapp | G06K 9/62 |
| | | | 382/131 |
| 2015/0363904 A1* | 12/2015 | Arai | G06T 5/003 |
| | | | 382/131 |

* cited by examiner

FIG. 5
HIGH DENSITY
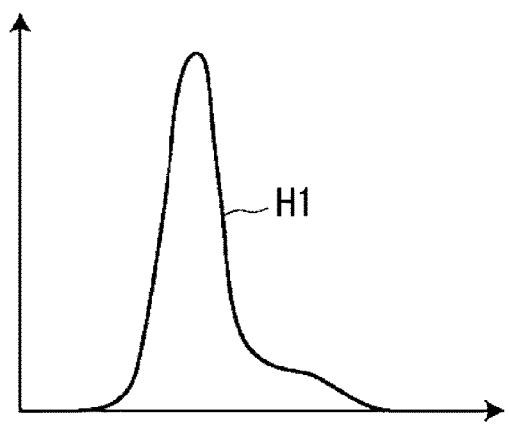
FAT
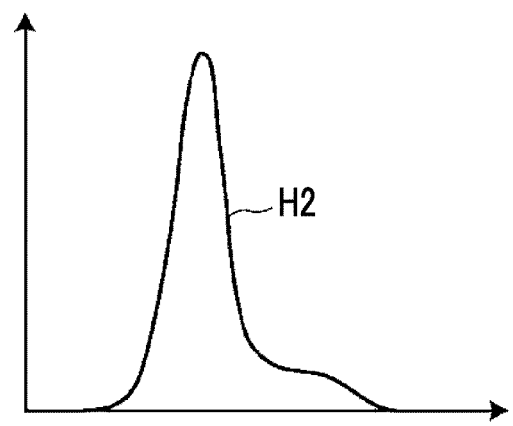
MAMMARY GLAND DISPERSED
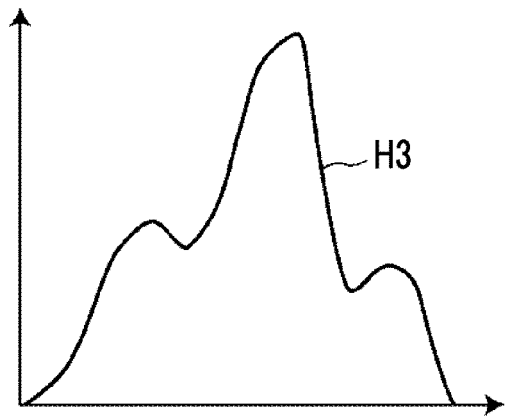
HETEROGENEOUS HIGH DENSITY
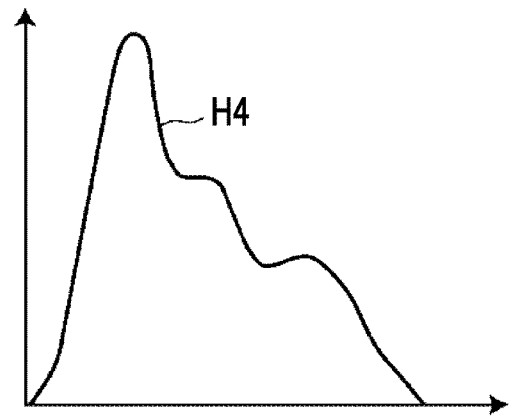

FIG. 6
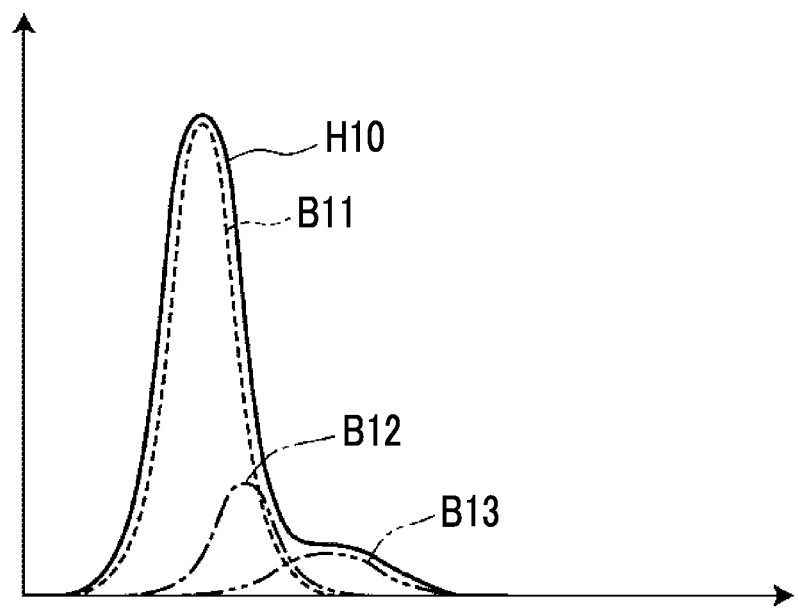
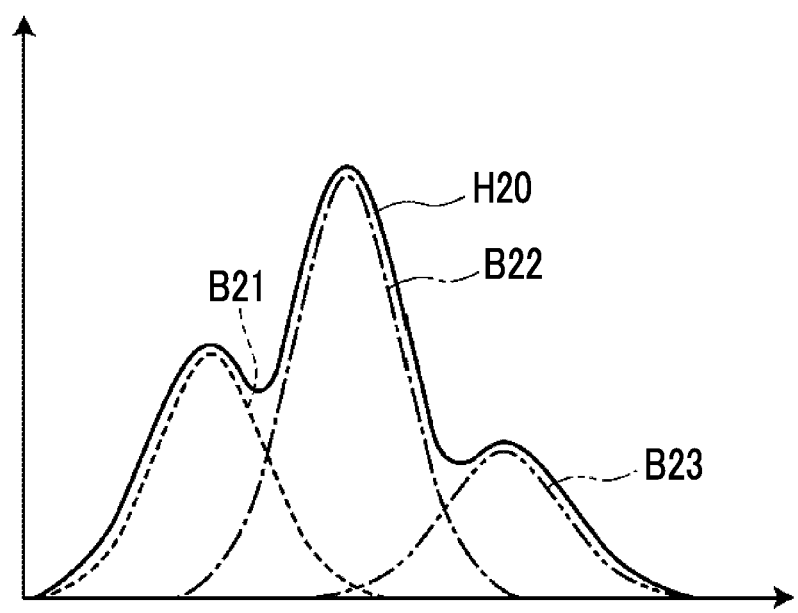

BREAST TYPE IDENTIFICATION DEVICE, METHOD, AND PROGRAM

CROSS REFERENCE TO RELATED APPLICATIONS

The present application claims priority under 35 U.S.C. § 119 to Japanese Patent Application No. 2017-187878 filed on Sep. 28, 2017. The above application is hereby expressly incorporated by reference, in its entirety, into the present application.

BACKGROUND

Field of the Invention

The present invention relates to a breast type identification device, method, and program for identifying the type of a breast based on a breast image obtained by imaging the breast with a mammography imaging apparatus.

Related Art

In recent years, in order to encourage the early detection of breast cancer, image diagnosis using a radiographic image capturing apparatus (called mammography) for imaging a breast has been drawing attention. In mammography, the breast is placed on an imaging table, and imaging is performed in a state in which the breast is compressed by a compression plate. The breast is mainly formed of mammary gland tissues and adipose tissues, and it is important for diagnosis to find lesions such as a tumor and calcification hidden in the mammary gland tissue. For this reason, a radiographic image (breast image) of the breast imaged by mammography is provided to a doctor for diagnosis after being subjected to image processing with a dedicated operation terminal or the like. The doctor examines the presence or absence of a lesion by displaying the breast image on a display and interpreting the breast image.

On the other hand, mammary gland tissues and adipose tissues are mixed in the breast. According to the ratio between mammary gland tissues and adipose tissues and the distribution of mammary gland tissues and adipose tissues, the breast can be classified into four breast types of high density type, fat type, mammary gland dispersed type, and inhomogeneous high density type. Breasts classified into the high density type, among these breast types, have uniform distribution of mammary gland tissues, and there is almost no mixture of fat. For this reason, it is difficult to detect a lesion based on a breast image. In order to accurately perform a diagnosis using a breast image acquired by imaging such a high density type breast, it is desired to perform image processing for increasing the contrast on the breast image of the high density type breast. For example, JP2006-263055A has proposed a method of performing image processing, such as processing for emphasizing the contrast, on the breast image according to the ratio between mammary gland tissues and adipose tissues in the breast, the distribution of mammary gland tissues and adipose tissues, and the like.

Here, it is conceivable to perform processing for emphasizing the contrast on the breast image regardless of the breast type. However, in a case where the processing for emphasizing the contrast is performed on a fat type breast image, graininess becomes worse or the contrast is excessively emphasized. As a result, there is a possibility that the image will have an image quality not suitable for diagnosis. Therefore, in order to perform the processing for emphasizing the contrast, it is necessary to identify that the breast is a high density type based on the breast image. However, since both the high density type breast and the fat type breast among the four types described above have a single composition, image of the high density type breast and the fat type breast are similar. For this reason, skill is required to distinguish between the high density type and the fat type from the view of the breast image.

On the other hand, depending on a diagnostic system using a breast image, imaging conditions cannot be acquired from the mammography imaging apparatus in some cases. For this reason, a method of identifying the breast type using only the breast image has been proposed. For example, JP2005-065857A has proposed a method of calculating a threshold value of density for separating fat and mammary gland based on the pixel values of fat and pectoral muscle included in a breast image, calculating a mammary gland region based on the calculated threshold value, and identifying the breast type based on the ratio of the mammary gland region to the breast region in the breast image.

In the method disclosed in JP2005-065857A, it is necessary to image the breast with the positioning including the pectoral muscle. Therefore, in a case where the breast image does not include the pectoral muscle, it is not possible to identify the breast type.

SUMMARY

The invention has been made in view of the above circumstances, and it is an object of the invention to identify the type of a breast using a breast image including only the breast.

A breast type identification device according to the invention comprises: a first detection unit that detects a breast region and a skin line from a breast image obtained by imaging a breast with radiation; a first index value acquisition unit that acquires a first index value indicating a single composition degree of the breast region; a second detection unit that detects a boundary between an adipose tissue and a mammary gland tissue in a predetermined range from the skin line toward an inside of the breast region in the breast image; a second index value acquisition unit that acquires a second index value indicating a degree of clogging of mammary glands with respect to the breast region based on at least one of a strength of the boundary or a distance from the skin line; and an identification unit that identifies a type of the breast based on the first and second index values.

The "breast region" is a region, in which a radiation transmission image of the breast is expressed by radiation transmitted through the breast, in the breast image, and is a region obtained by excluding a direct radiation region, which is obtained by directly irradiating a detector with radiation at the time of imaging, from the breast image.

The "skin line" means a boundary line between the skin and the background in the breast image.

The "first index value indicating the single composition degree" is an index value indicating the extent to which the breast region has only one composition. The first index value becomes larger (or smaller) as the breast region becomes closer to a single composition.

The "second index value indicating the degree of clogging of mammary glands" is an index value indicating how many mammary glands are included in the breast region. The second index value increases (or decreases) as the amount of included mammary glands increases.

In the breast type identification device according to the invention, the first index value acquisition unit may acquire the first index value based on a histogram in the breast region.

In the breast type identification device according to the invention, the second detection unit may generate a line profile at a plurality of positions from the skin line toward the inside of the breast region, and detect a position where a signal value changes with a peak in the line profile as the boundary.

In the breast type identification device according to the invention, the second index value acquisition unit may acquire the second index value by multiplying an index value indicating the strength of the boundary by a weight coefficient based on the distance from the skin line in each of a plurality of the line profiles and adding an index value indicating the strength of the boundary after being multiplied by the weighting coefficient for each of the plurality of the line profiles.

The breast type identification device according to the invention may further comprise a display controller that displays the type of the breast on a display unit.

In the breast type identification device according to the invention, the display controller may further perform warning display according to the type of the breast.

A breast type identification method according to the invention comprises: detecting a breast region and a skin line from a breast image obtained by imaging a breast with radiation; acquiring a first index value indicating a single composition degree of the breast region; detecting a boundary between an adipose tissue and a mammary gland tissue in a predetermined range from the skin line toward an inside of the breast region in the breast image; acquiring a second index value indicating a degree of clogging of mammary glands with respect to the breast region based on at least one of a strength of the boundary or a distance from the skin line; and identifying a type of the breast based on the first and second index values.

In addition, a program causing a computer to execute the breast type identification method according to the present invention may be provided.

Another breast type identification device according to the invention comprises: a memory that stores commands to be executed by a computer; and a processor configured to execute the stored commands. The processor executes: processing for detecting a breast region and a skin line from a breast image obtained by imaging a breast with radiation; processing for acquiring a first index value indicating a single composition degree of the breast region; processing for detecting a boundary between an adipose tissue and a mammary gland tissue in a predetermined range from the skin line toward an inside of the breast region in the breast image; processing for acquiring a second index value indicating a degree of clogging of mammary glands with respect to the breast region based on at least one of a strength of the boundary or a distance from the skin line; and processing for identifying a type of the breast based on the first and second index values.

According to the invention, the first index value indicating the single composition degree of the breast region detected from the breast image is acquired, the second index value indicating the degree of clogging of mammary glands with respect to the breast region is acquired based on at least one of the strength of the boundary between the adipose tissue and the mammary gland tissue or the distance from the skin line, and the breast type is identified based on the first and second index values. Therefore, even in a case where tissues other than the breast are included in the breast image, it is possible to identify the breast type.

BRIEF DESCRIPTION OF THE DRAWINGS

FIG. 5 is a diagram showing a histogram according to the breast type.

FIG. 6 is a diagram illustrating an approximation in the mixed Gaussian distributions of a histogram.

DETAILED DESCRIPTION

Figure 1:
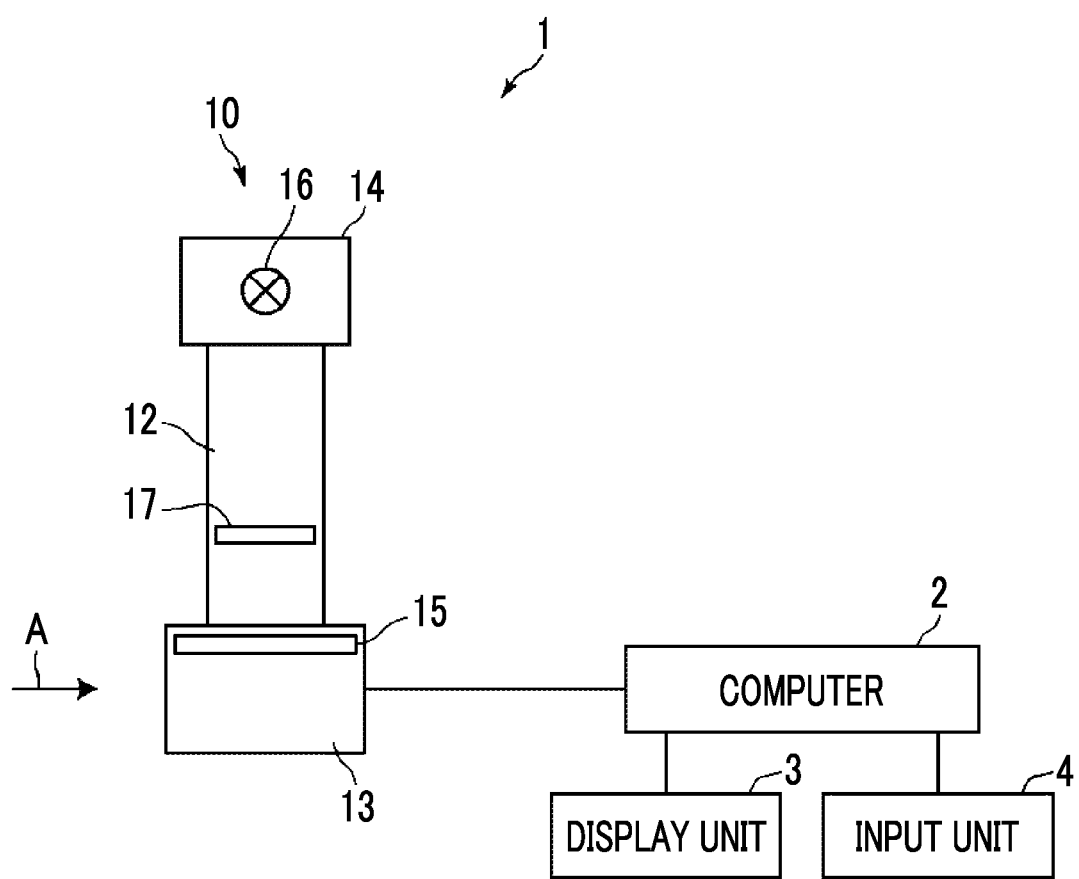
FIG. 1 is a schematic configuration diagram of a radiographic image capturing apparatus to which a breast type identification device according to a first embodiment of the invention is applied.
Figure 2:
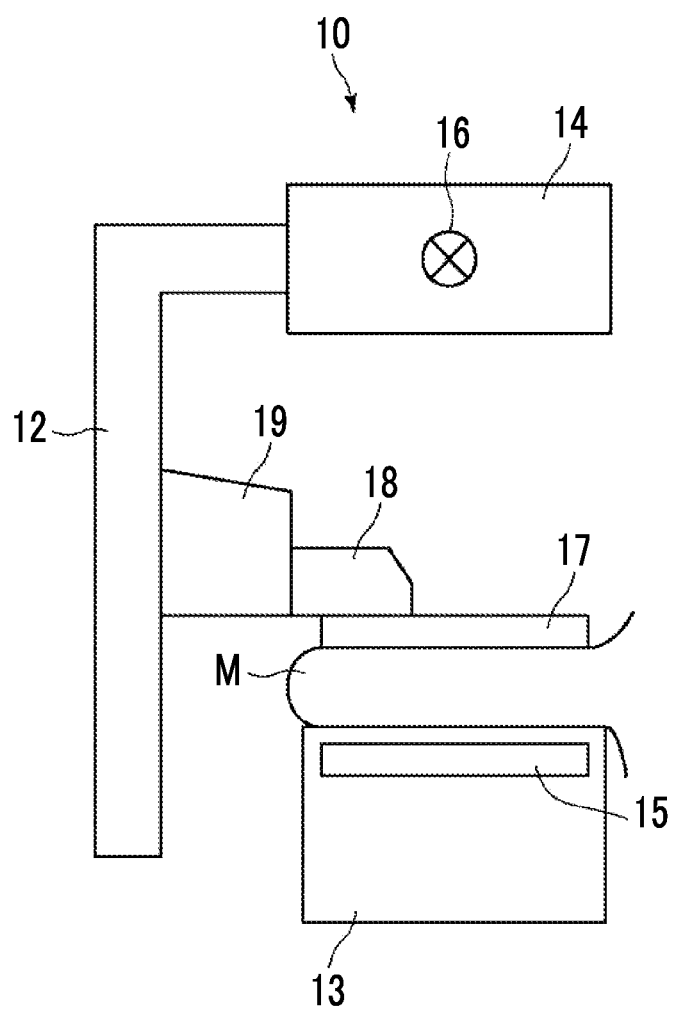
FIG. 2 is a diagram of the radiographic image capturing apparatus as viewed from the direction of arrow A in FIG. 1.

Hereinafter, embodiments of the invention will be described with reference to the accompanying diagrams. FIG. 1 is a schematic configuration diagram of a radiographic image capturing apparatus to which a breast type identification device according to a first embodiment of the invention is applied, and FIG. 2 is a diagram of the radiographic image capturing apparatus as viewed from the direction of arrow A in FIG. 1. A radiographic image capturing apparatus 1 is a mammography apparatus that captures an image of a breast M that is a subject. As shown in FIG. 1, the radiographic image capturing apparatus 1 includes an imaging unit 10, a computer 2 connected to the imaging unit 10, and a display unit 3 and an input unit 4 connected to the computer 2.

The imaging unit 10 includes an arm unit 12. An imaging table 13 is attached to one end portion of the arm unit 12, and an irradiation unit 14 is attached to the other end portion so as to face the imaging table 13.

A radiation detector 15, such as a flat panel detector, is provided inside the imaging table 13. In addition, a circuit board on which a charge amplifier for converting a charge signal read from the radiation detector 15 into a voltage signal, a sampling two correlation pile circuit for sampling a voltage signal output from the charge amplifier, an AD conversion unit for converting a voltage signal into a digital signal, and the like are provided is provided inside the imaging table 13.

The radiation detector 15 can perform recording and reading of a radiographic image repeatedly. A so-called direct type radiation detector that generates an electric charge by direct reception of radiation may be used, or a so-called indirect type radiation detector that converts radiation into visible light and then converts the visible light into a charge signal may be used. As a method of reading a radiographic image signal, it is desirable to use a so-called TFT reading method in which a radiographic image signal is read by ON and OFF of a thin film transistor (TFT) switch or a so-called optical reading method in which a radiographic image signal is read by emission of reading light. However, other methods may also be used without being limited to the above methods.

An X-ray source 16, which is a radiation source, is housed inside the irradiation unit 14. The timing of emission of X-rays, which are radiations from the X-ray source 16, and X-ray generation conditions in the X-ray source 16, that is, imaging conditions such as a tube voltage and a mAs value, are controlled by the computer 2.

A compression plate 17 disposed above the imaging table 13 in order to compress the breast M, a support unit 18 for supporting the compression plate 17, and a moving mechanism 19 for moving the support unit 18 in the vertical direction in FIGS. 1 and 2 are provided in the arm unit 12. Information of the height of the compression plate 17, which is a distance between the compression plate 17 and the imaging table 13, is input to the computer 2.

The display unit 3 is a display device, such as a cathode ray tube (CRT) or a liquid crystal monitor, and displays a breast image that is an X-ray image of the breast M acquired as will be described later, a message required for the operation, and the like. The display unit 3 may include a speaker to output sound.

The input unit 4 is a keyboard, a mouse, or a touch panel type input device, and receives an operation on the radiographic image capturing apparatus 1 by the operator. In addition, the input unit 4 receives an input of various kinds of information, such as imaging conditions, and an instruction to modify the information, which are required to perform imaging. In the present embodiment, each unit of the radiographic image capturing apparatus 1 operates according to the information input from the input unit 4 by the operator.

A breast type identification program is installed on the computer 2. In the present embodiment, the computer may be a workstation or a personal computer that is directly operated by the operator, or may be a server computer connected to these through a network. The energy subtraction processing program is distributed by being recorded on a recording medium, such as a digital versatile disc (DVD) and a compact disc read only memory (CD-ROM), and is installed on the computer from the recording medium. Alternatively, the energy subtraction processing program is stored in a storage device of a server computer connected to the network or in a network storage so as to be accessible from the outside, and is downloaded and installed on the computer as necessary.

Figure 3:
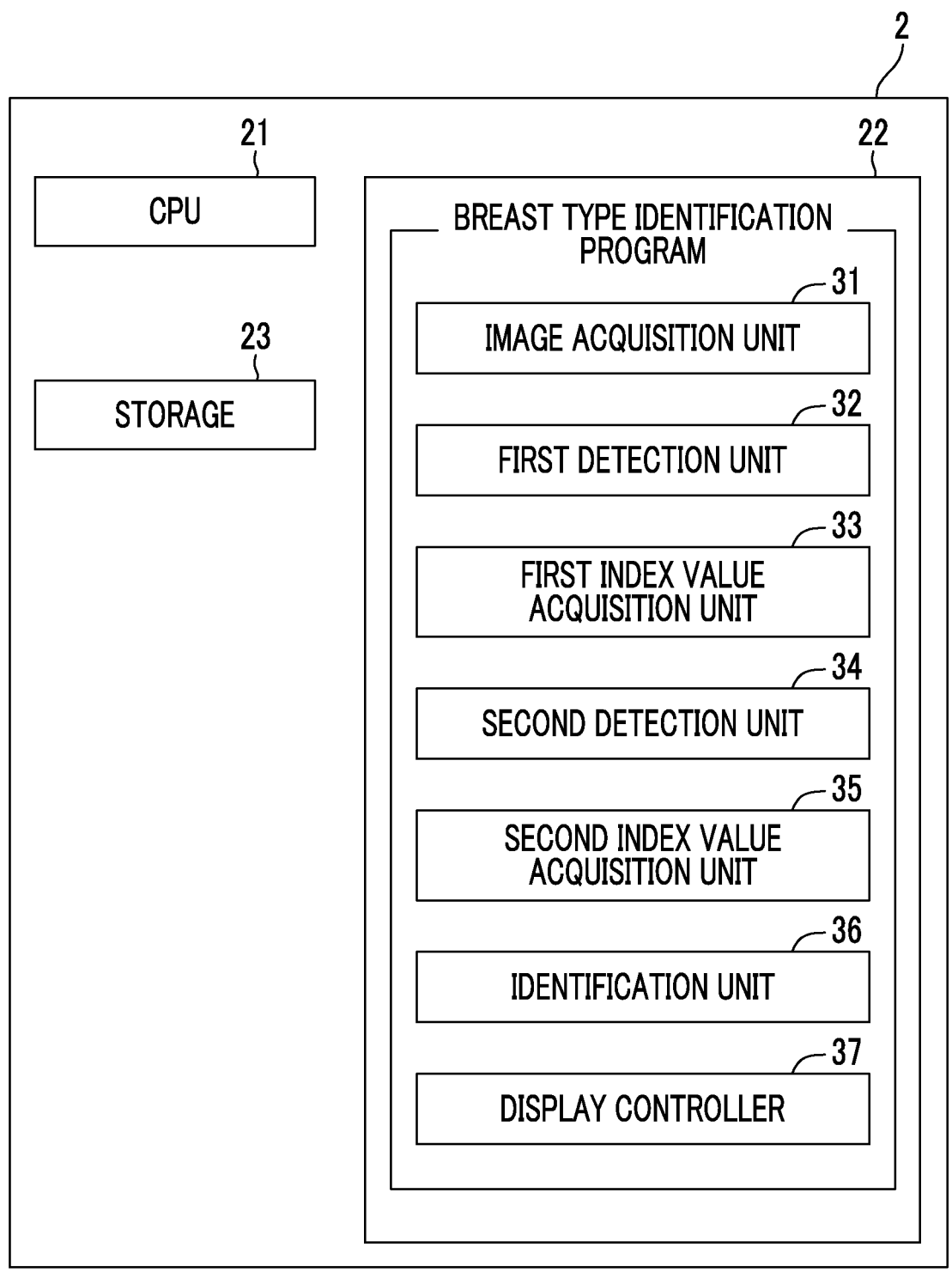
FIG. 3 is a diagram showing the schematic configuration of the breast type identification device according to the first embodiment.

FIG. 3 is a diagram showing the schematic configuration of the breast type identification device according to the first embodiment realized by installing a breast type identification program on the computer 2. As shown in FIG. 3, the breast type identification device according to the first embodiment includes a central processing unit (CPU) 21, a memory 22, and a storage 23 as the configuration of a standard computer.

The storage 23 is a storage device, such as a hard disk or a solid state drive (SSD), and stores various kinds of information required for processing including a program for driving each unit of the radiographic image capturing apparatus 1 and a breast type identification program. A breast image acquired by imaging is also stored in the storage 23.

The memory 22 temporarily stores the breast type identification program and the like stored in the storage 23 so that the CPU 21 executes various kinds of processing. As processing to be executed by the CPU 21, the breast type identification program defines: image acquisition processing for acquiring a breast image by causing the radiographic image capturing apparatus 1 to perform X-ray imaging; first detection processing for detecting a breast region and a skin line from the breast image; first index value acquisition processing for acquiring a first index value indicating the single composition degree of the breast region; second detection processing for detecting a boundary between adipose tissue and mammary gland tissue in a predetermined range from the skin line toward the inside of the breast region in the breast image; second index value acquisition processing for acquiring a second index value indicating a degree of clogging of mammary glands with respect to the breast region based on at least one of the strength of the boundary or the distance from the skin line; identification processing for identifying the breast type based on the first and second index values; and display control processing for displaying an identification result of the breast type on the display unit 3.

The CPU 21 executes these processes according to the breast type identification program, so that the computer 2 functions as an image acquisition unit 31, a first detection unit 32, a first index value acquisition unit 33, a second detection unit 34, a second index value acquisition unit 35, an identification unit 36, and a display controller 37. The present embodiment is not limited to executing the function of each unit by the software configuration according to the breast type identification program. For example, the function of each unit may be executed only by the hardware configuration, such as a plurality of integrated circuits (ICs), processors, application specific integrated circuits (ASICs), field-programmable gate arrays (FPGAs), memories, and a combination thereof. Alternatively, the processing of each unit may be executed by the combination of the software configuration and the hardware configuration.

The image acquisition unit 31 acquires a breast image G0 by controlling the irradiation unit 14 according to predetermined imaging conditions. Specifically, X-rays are emitted to the breast M by driving the X-ray source 16 according to the predetermined imaging conditions, and X-rays transmitted through the breast M are detected by the radiation detector 15, thereby acquiring the breast image G0.

Figure 4:
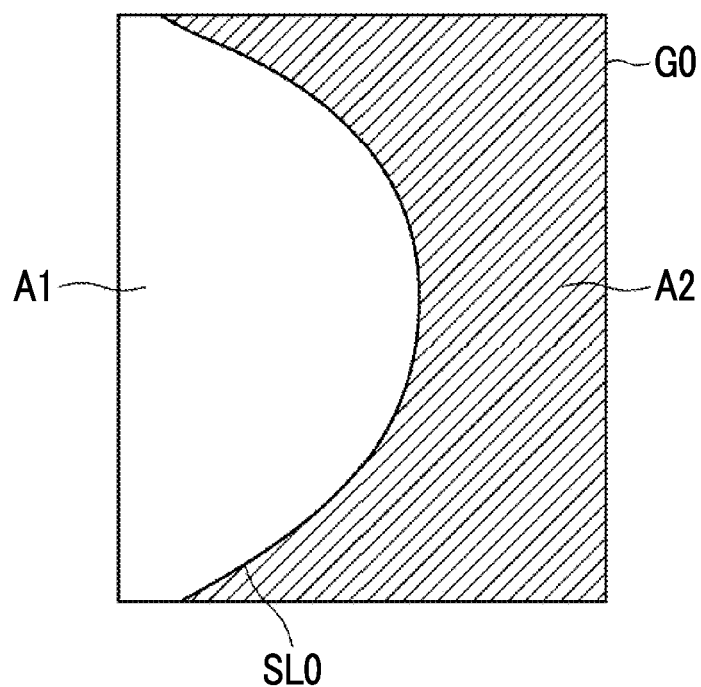
FIG. 4 is a diagram illustrating the detection of a breast region and a skin line.

The first detection unit 32 detects a breast region and a skin line from the breast image G0. FIG. 4 is a diagram illustrating the detection of the breast region and the skin line. As shown in FIG. 4, the breast image G0 includes a breast region A1 and a direct radiation region A2 corresponding to a region where X-rays are directly emitted to the radiation detector 15. Here, the direct radiation region A2 has a higher density than the breast region A1. Therefore, the first detection unit 32 detects the breast region A1 from the breast image G0 by performing threshold value processing using a threshold value for distinguishing between the breast region A1 and the direct radiation region A2. The boundary between the detected breast region A1 and the direct radiation region A2 is detected as a skin line SL0.

The first index value acquisition unit 33 acquires a first index value indicating the single composition degree of the breast region A1. The first index value indicating the single composition degree is an index value indicating the extent to which the breast region A1 has only one composition. For this reason, the first index value acquisition unit 33 generates a histogram of the breast region A1 detected from the breast image G0. FIG. 5 is a diagram showing a histogram according to the breast type. FIG. 5 shows histograms H1 to H4 for four breast types of high density type, fat type, mammary gland dispersed type, and inhomogeneous high density type.

In the high density type breast, since a large amount of mammary glands are included in the breast region A1, the composition is substantially single. Therefore, the histogram H1 of the high density type has a unimodal distribution including only one peak. In the fat type breast, since a large amount of fat is included in the breast region A1, the composition is substantially single. Therefore, the histogram H2 of the fat type has a unimodal distribution including only one peak.

On the other hand, in the mammary gland dispersed type breast and the inhomogeneous high density type breast, both the mammary gland and the fat are mixed in the breast region A1. For this reason, each of the mammary gland dispersed type breast and the inhomogeneous high density type breast has a plurality of compositions. Therefore, each of the histograms H3 and H4 of the mammary gland dispersed type and the inhomogeneous high density type has a multimodal distribution including a plurality of peaks.

The first index value acquisition unit 33 includes a discriminator for acquiring the single composition degree of the breast region A1 as a first index value. The discriminator is generated by performing machine learning with histograms of a large number of single composition breast regions and histograms of non-single composition breast regions as teacher data. As a method of machine learning, any method, for example, AdaBoost and support vector machine can be used.

In machine learning, a histogram used for learning is approximated by the mixed Gaussian distribution. FIG. 6 is a diagram illustrating an approximation in the mixed Gaussian distribution of a histogram. A histogram H10 having a unimodal distribution shown on the upper side of FIG. 6 is approximated by a Gaussian distribution B11 shown by a broken line, a Gaussian distribution B12 shown by a one-dot chain line, and a Gaussian distribution B13 shown by a two-dot chain line. A histogram H20 having a multimodal distribution shown on the lower side of FIG. 6 is approximated by a Gaussian distribution B21 shown by a broken line, a Gaussian distribution B22 shown by a one-dot chain line, and a Gaussian distribution B23 shown by a two-dot chain line.

In the discriminator, learning is performed so as to output a larger value as the distribution of a histogram becomes closer to the unimodal shape with parameters of the Gaussian distribution in the histogram, which is teacher data, as its input. In the present embodiment, therefore, the first index value becomes larger as the breast region A1 becomes closer to a single composition. As the parameters of the Gaussian distribution, the average value, variance, and the like of the Gaussian distribution are used. In a case where the histogram of the breast region A1 is input to the discriminator learned in this manner, the first index value indicating the single composition degree of the breast region A1 is output. In acquiring the first index value, the input histogram of the breast region A1 is approximated by the mixed Gaussian distribution as in the case of learning, and a parameter of the Gaussian distribution obtained by approximating the histogram is input to the discriminator.

The second detection unit 34 detects a boundary between the adipose tissue and the mammary gland tissue in a predetermined range from the skin line SL0 toward the inside of the breast region A1 in the breast image G0. Specifically, a line profile is generated at a plurality of positions from the skin line SL0 toward the inside of the breast region A1, and a position where the signal value changes with a peak in the line profile is detected as a boundary between the adipose tissue and the mammary gland tissue.

Figure 7:
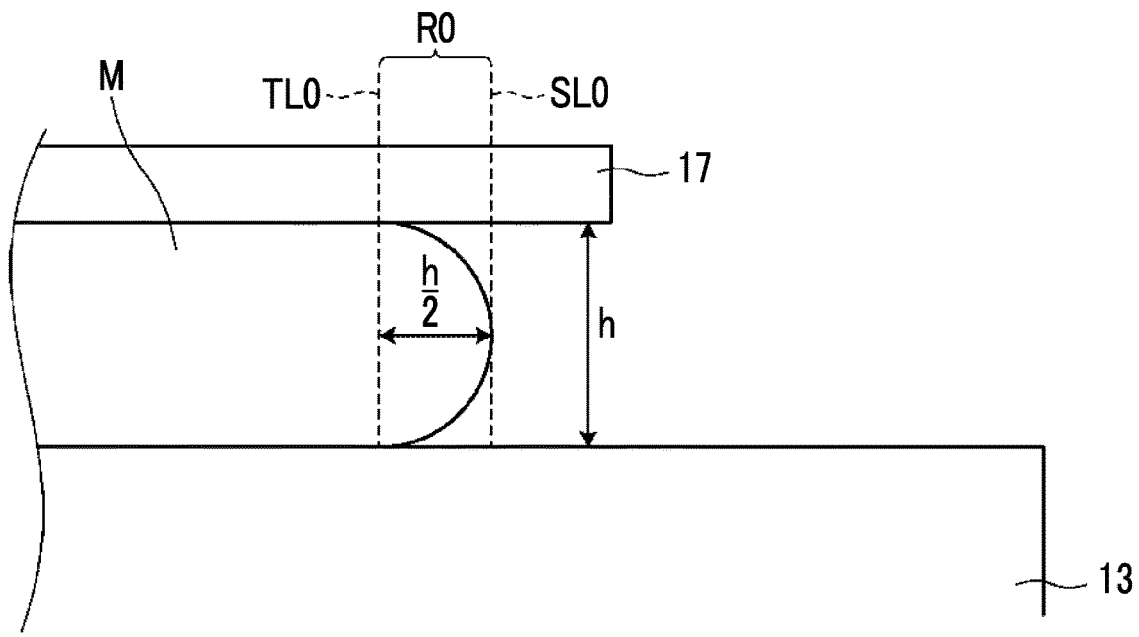
FIG. 7 is a diagram showing a breast interposed between a compression plate and an imaging table.
Figure 8:
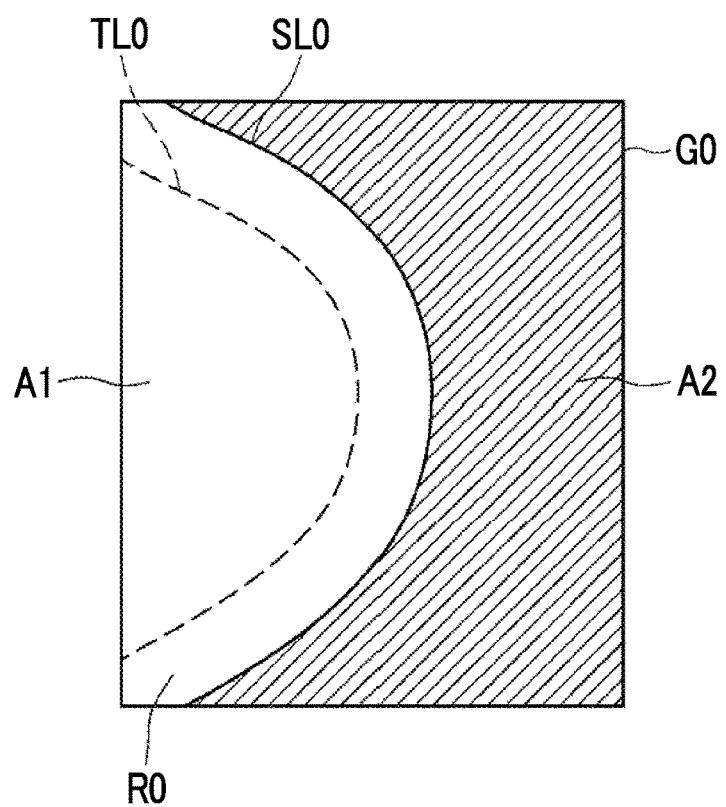
FIG. 8 is a diagram illustrating the setting of a predetermined range from the skin line in a breast image.

For this reason, the second detection unit 34 sets a predetermined range from the skin line SL0 in the breast image G0. FIG. 7 is a diagram showing a breast interposed between the compression plate 17 and the imaging table 13, and FIG. 8 is a diagram illustrating the setting of a predetermined range from the skin line SL0 in the breast image G0. At the time of imaging, the breast M is interposed between the imaging table 13 and the compression plate 17 as shown in FIG. 7. Therefore, in the breast image G0 acquired by imaging, a region corresponding to a part in contact with neither the imaging table 13 nor the compression plate 17 in the breast M is present toward the inside of the breast region A1 from the skin line SL0.

The second detection unit 34 acquires information of the height of the compression plate 17 from the imaging unit 10. Here, it is assumed that the cross-sectional shape of the breast M in the vicinity of the skin line SL0 of the breast M is semicircular. In this case, assuming that the height of the compression plate 17 is h, the breast M comes into contact with the compression plate 17 and the imaging table 13 at a point where the distance from the skin line SL0 is h/2 in the breast region A1 of the breast image G0. The second detection unit 34 sets a line TL0 configured to include a plurality of points where the distance from the skin line SL0 is h/2. Then, as shown in FIGS. 7 and 8, a region between the skin line SL0 and the line TL0 in the breast region A1 is set as a predetermined range RO from the skin line SL0 in the breast image G0.

As a distance between the skin line SL0 and the line TL0 for setting the predetermined range RO, a predetermined value statistically calculated so that the line TL0 is located within the mammary gland region in the breast region A1 may be used.

Figure 9:
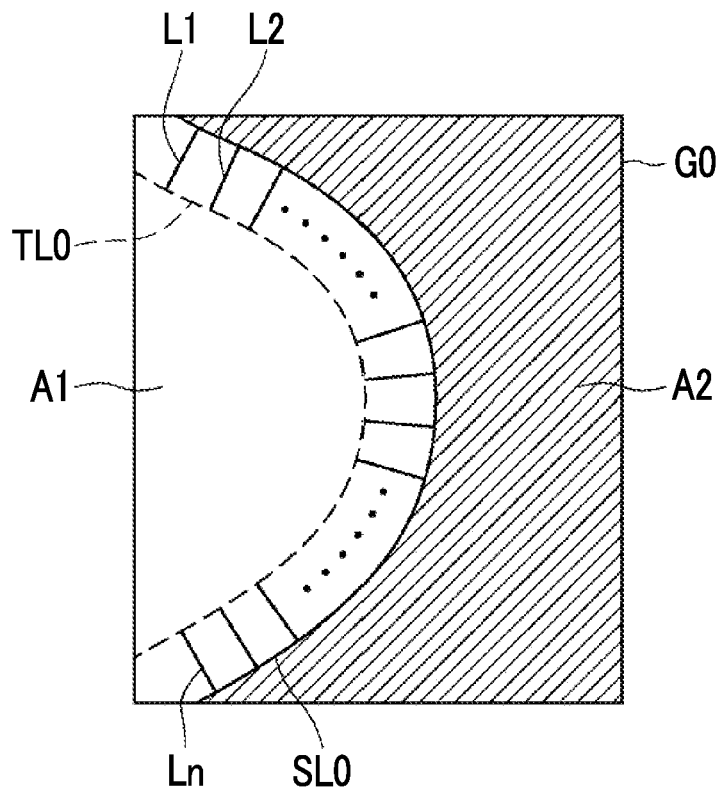
FIG. 9 is a diagram showing a plurality of lines set in the breast image.

The second detection unit 34 sets a plurality of predetermined reference points on the skin line SL0 at equal intervals. The number of reference points may be, for example, 40, but is not limited thereto. Then, a plurality of lines having each reference point as a start position and a point on the line TL0 closest to each reference point as an end position are set in the breast image G0. FIG. 9 is a diagram showing lines set in the breast image G0. Then, the second detection unit 34 generates a line profile for each line.

The line profile is normalized by the following Equation (1) in order to prevent a variation in the value according to the thickness of the breast M. Here, Lsi(x, y) is a normalized pixel value on the line Li, and Li(x, y) is a pixel value before normalization on the line Li. The skin line pixel value is the maximum value of the pixel value on the skin line SL0 in the breast image G0. The skin line pixel value is a maximum value that each line Li can take on the line profile.

Figure 10:
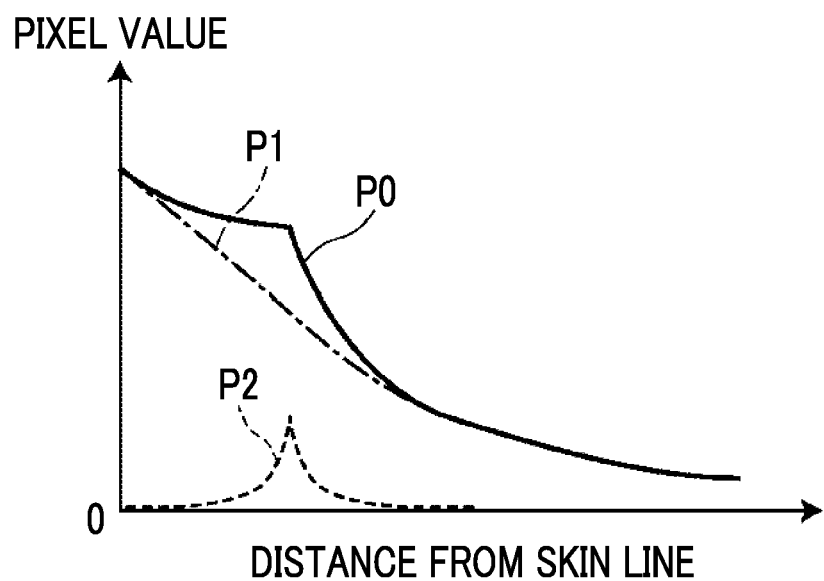
FIG. 10 is a diagram showing a line profile.

The mammary gland pixel value is a pixel value of a pixel having a maximum mammary gland content rate in the breast image G0. In order to calculate the mammary gland content rate, for example, a method disclosed in JP2010-253245A can be used. The method described in JP2010-253245A is a method in which, in mammography, the mammary gland content rate is calculated based on the relationship among the X-ray dose directly reaching a radiation detector without being transmitted through the breast as a subject, the X-ray dose reaching the radiation detector after being transmitted through the breast, an X-ray attenuation coefficient due to fat, an X-ray attenuation coefficient due to mammary gland, and the thickness of the breast. The mammary gland pixel value is a minimum value that each line Li can take on the line profile. FIG. 10 is a diagram showing a line profile.

$$Lsi(x,y)=(Li(x,y)-\text{mammary gland pixel value})/(\text{skin line pixel value}-\text{mammary gland pixel value}) \quad (1)$$

Figure 11:
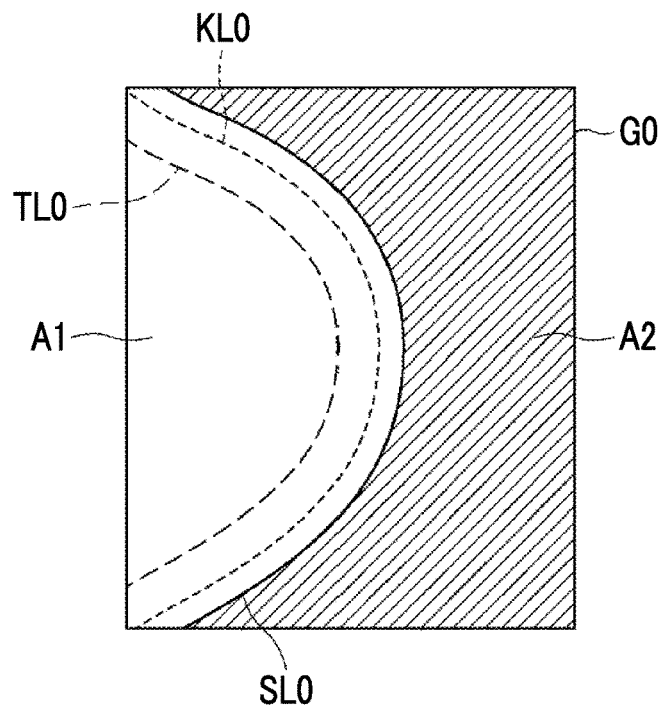
FIG. 11 is a diagram showing a boundary line between the adipose tissue and the mammary gland tissue in the breast image.

The second detection unit 34 further smoothes each line profile P0. Specifically, the line profile P0 is smoothed by calculating the average value of pixel values of a plurality of adjacent pixels. The number of pixels for calculating the average value can be, for example, 5 pixels, but is not limited thereto. A smoothed line profile P1 is shown by a one-dot chain line in FIG. 10. Then, the second detection unit 34 calculates a difference value P2 between the line profiles by subtracting the smoothed line profile P1 from the line profile P0 before smoothing. The difference value P2 between the line profiles is shown by a broken line in FIG. 10. As shown in FIG. 10, a peak that is convex upward appears in the difference value P2 between the line profiles. The position of this peak corresponds to a position where the signal value in the line profile P0 changes. The second detection unit 34 detects the peak position of the difference value P2 between the line profiles, that is, the position where the signal value of the line profile P0 changes with a peak, as a boundary between the adipose tissue and the mammary gland tissue in the breast region A1. By interpolating the boundary detected in each line Li between the lines Li, as shown in FIG. 11, a boundary line KL0 between the adipose tissue and the mammary gland tissue can be shown in the breast image G0.

Figure 12:
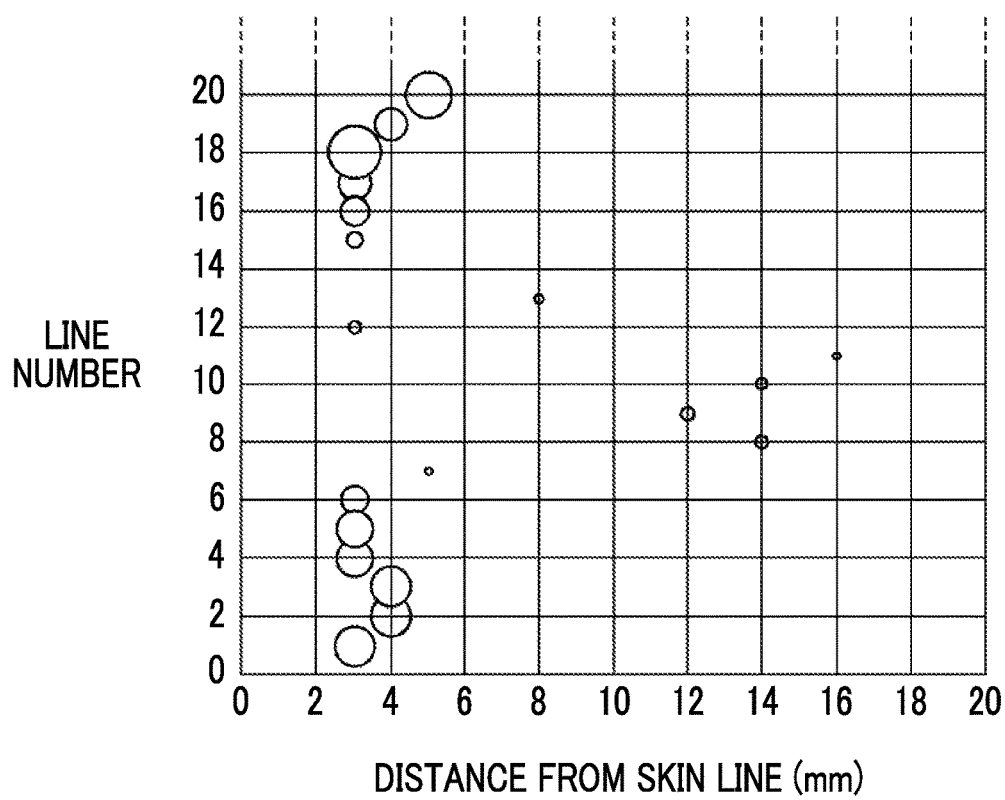
FIG. 12 is a diagram showing a mapping result of a strength index value and a distance of the skin line from the boundary.
Figure 13:
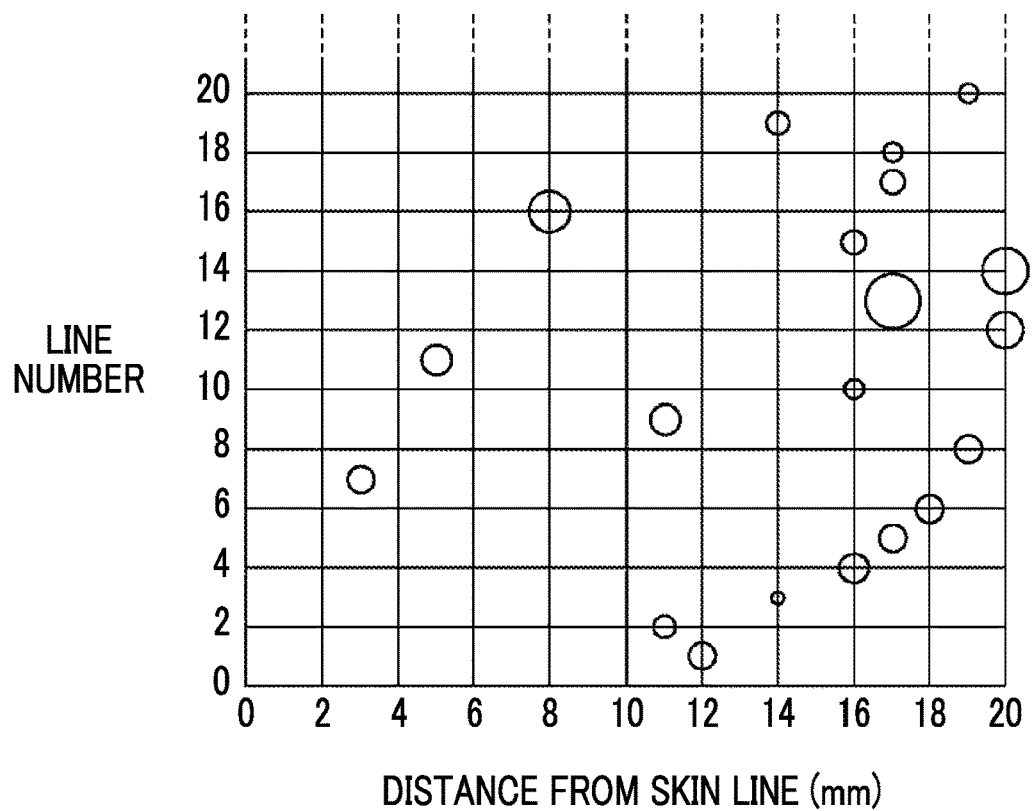
FIG. 13 is a diagram showing a mapping result of a strength index value and a distance of the skin line from the boundary.

The second index value acquisition unit 35 acquires a second index value indicating the degree of clogging of mammary glands with respect to the breast region A1. The second index value is an index value indicating how many mammary glands are included. In the present embodiment, the second index value increases as the amount of included mammary glands increases. In order to acquire the second index value, the second index value acquisition unit 35 maps the index value indicating the strength of the boundary between the adipose tissue and the mammary gland tissue and the distance from the skin line SL0 of the boundary, which have been detected by the second detection unit 34, for each line Li. As the index value indicating the strength of the boundary (hereinafter, referred to as a strength index value), the value of the peak position of the difference value P2 between the line profiles, which is calculated in a case where the second detection unit 34 detects the boundary between the adipose tissue and the mammary gland tissue, is used. FIGS. 12 and 13 are diagrams showing mapping results of the strength index value and the distance from the skin line SL0 of the boundary. Although the mapping is expressed in a three-dimensional space, the mapping result is shown in a two-dimensional space in which the magnitude of the strength index value is expressed as the size of a circle for the sake of explanation. In addition, in FIGS. 12 and 13, the number of lines is shown up to 20 for the sake of explanation. Here, as the strength index value becomes larger, the boundary between the adipose tissue and the mammary gland tissue is more clearly expressed in the breast image G0.

In the mapping shown in FIG. 12, relatively large strength index values are distributed in a narrow range of 3 to 5 mm from the skin line SL0. On the other hand, in the mapping shown in FIG. 13, relatively large strength index values are present but distributed over a wide range from the skin line SL0.

The second index value acquisition unit 35 acquires the second index value by multiplying the strength index value in each line by a weighting coefficient based on the matching of the distance from the skin line SL0 of the boundary and adding a strength index value after being multiplied by the weighting coefficient. The weighting coefficient based on the matching of the distance from the skin line is set as follows. That is, the position of a boundary for a certain line Li is compared with the position of a boundary for an adjacent line, for example, a line Li+1 of the next number, and the weighting coefficient is set so as to become larger as the position of the boundary with the adjacent line Li+1 becomes closer. For example, the weighting coefficient is set to 1.0 in a case where the position of the boundary with the adjacent line Li+1 matches, and the weighting coefficient becomes smaller as the position of the boundary with the adjacent line Li+1 becomes farther.

In a case where the second index value is acquired as described above, in a case where the boundary between the adipose tissue and the mammary gland tissue is clearly shown and is continuous in the breast image G0, the second index value increases. In a case where the mapped breast image shown in FIG. 12 is compared with the mapped breast image shown in FIG. 13, the second index value in the mapped breast image shown in FIG. 12 is larger.

The identification unit 36 identifies the breast type based on the first and second index values. Specifically, a first determination regarding whether or not the first index value is equal to or greater than a predetermined threshold value Th1 is performed, and a second determination regarding whether or not the second index value is equal to or greater than a predetermined threshold value Th2 is performed. Here, in a case where the first index value is equal to or greater than the threshold value Th1, the single composition degree is large. Therefore, the breast type can be identified as either the high density type or the fat type. On the other hand, in the case of the high density type, in the breast region A1 of the breast image G0, the boundary between the fat region and the mammary gland region is clearly and continuously present in the skin line SL0. Conversely, in the case of the fat type, there is no clear boundary between the fat region and the mammary gland region. Therefore, in a case where the second index value in the high density type breast is compared with the second index value in the fat type breast, the second index value in the high density type breast is larger.

On the other hand, in a case where the first index value is less than the threshold value Th1, the breast type can be identified as either the mammary gland dispersed type or the inhomogeneous high density type. In the case of the inhomogeneous high density type, in the breast region A1 of the breast image G0, the boundary between the fat region and the mammary gland region is clearly and continuously present in the skin line SL0. Conversely, in the case of the mammary gland dispersed type, there is no clear boundary between the fat region and the mammary gland region. Therefore, in a case where the second index value in the mammary gland dispersed type breast is compared with the second index value in the inhomogeneous high density type, the second index value in the inhomogeneous high density type breast is larger.

Accordingly, the identification unit 36 identifies the breast type as follows according to the first and second determination results.

First index value ≥Th1 and second index value ≥Th2 . . . High density type

First index value ≥Th1 and second index value <Th2 . . . Fat type

Figure 14:
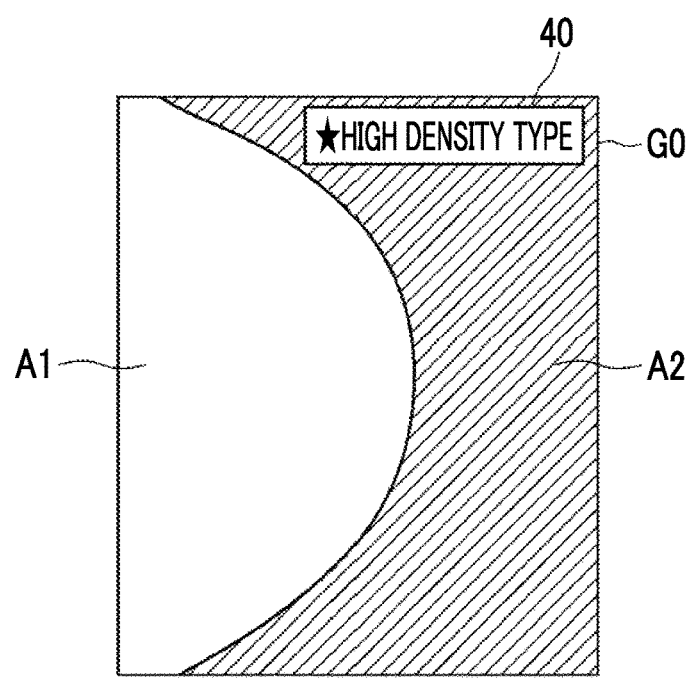
FIG. 14 is a diagram showing a breast image in which the breast type is displayed and a warning is displayed.

First index value <Th1 and second index value ≥Th2 . . . Inhomogeneous high density type First index value <Th1 and second index value <Th2 . . . Mammary gland dispersed type The display controller 37 displays the breast type identified by the identification unit 36 on the display unit 3. In the case of the high density type among the four breast types, since a lesion is likely to be overlooked in image diagnosis, it is desired to combine a method other than image diagnosis, such as ultrasound examination. Therefore, in a case where the breast type identified by the identification unit 36 is a high density type, it is preferable to display a warning. As a warning display, for example, it is conceivable to change the color of characters displayed on the display unit 3, to display characters to be displayed so as to flicker, or to give a mark only in a case where the breast type is identified as a high density type. FIG. 14 is a diagram showing a breast type displayed on the display unit 3. As shown in FIG. 14, the identified breast type (in FIG. 14, high density type) is displayed in the direct radiation region A2 of the breast image G0. In addition, there is a warning display 40 using a star mark on the left side of the characters of the high density type.

Figure 15:
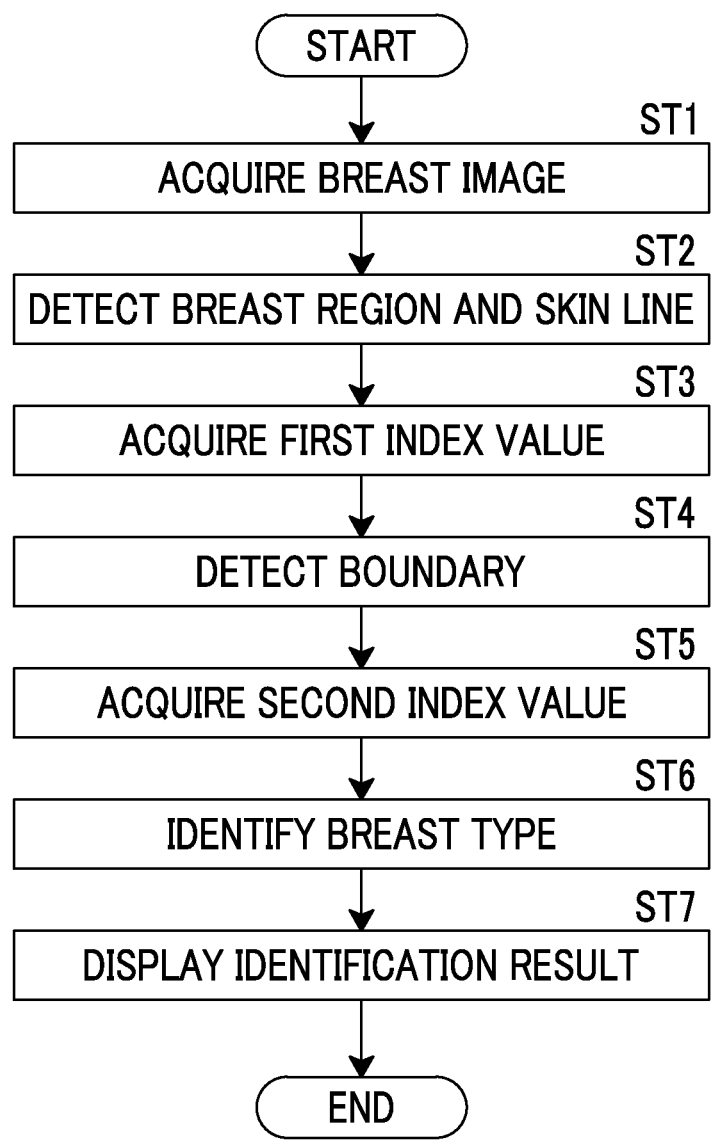
FIG. 15 is a flowchart showing the process performed in the first embodiment.

Next, a process performed in the present embodiment will be described. FIG. 15 is a flowchart showing the process performed in the first embodiment. In a case where the input unit 4 receives an operator's instruction to start the process, the breast M is imaged, and the image acquisition unit 31 acquires the breast image G0 (step ST1). Then, the first detection unit 32 detects the breast region A1 and the skin line SL0 from the breast image G0 (step ST2), and the first index value acquisition unit 33 acquires the first index value indicating the single composition degree of the breast region A1 (step ST3).

Then, the second detection unit 34 detects a boundary between the adipose tissue and the mammary gland tissue in the predetermined range RO from the skin line SL0 toward the inside of the breast region A1 in the breast image G0 (step ST4). Then, based on at least one of the strength of the boundary or the distance from the skin line, the second index value acquisition unit 35 acquires a second index value indicating the degree of clogging of mammary glands with respect to the breast region A1 (step ST5). Then, the identification unit 36 identifies the breast type based on the first and second index values (step ST6), and the display controller 37 displays the identification result of the breast type on the display unit 3 (step ST7). Then, the process ends.

As described above, in the present embodiment, the first index value indicating the single composition degree of the breast region A1 detected from the breast image G0 is acquired, the second index value indicating the degree of clogging of mammary glands with respect to the breast region A1 is acquired based on at least one of the strength of the boundary between the adipose tissue and the mammary gland tissue or the distance from the skin line, and the breast type is identified based on the first and second index values. Therefore, even in a case where tissues other than the breast are included in the breast image G0, it is possible to identify the breast type.

Figure 16:
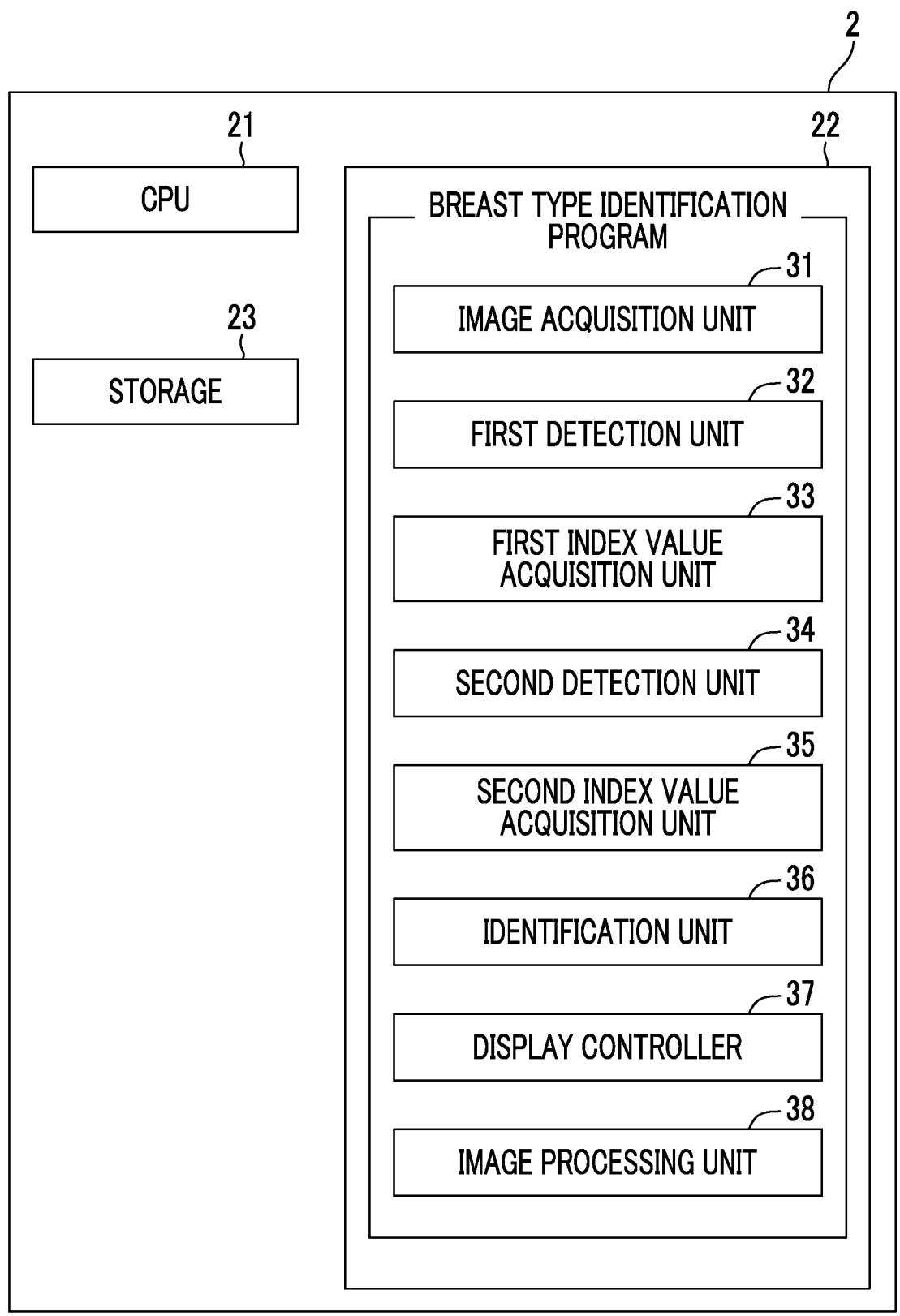
FIG. 16 is a diagram showing the schematic configuration of a breast type identification device according to a second embodiment.

Next, a second embodiment of the present invention will be described. FIG. 16 is a diagram showing the schematic configuration of a breast type identification device according to a second embodiment of the invention. In FIG. 16, the same components as in FIG. 3 are denoted by the same reference numbers, and the detailed explanation thereof will be omitted herein. The breast type identification device according to the second embodiment is different from the breast type identification device according to the first embodiment in that an image processing unit 38 that performs image processing according to the identified breast type on the breast image G0 is provided.

Here, breasts classified into the high density type have uniform distribution of mammary gland tissues, and there is almost no mixture of fat. For this reason, it is difficult to detect a lesion based on the breast image G0. In the second embodiment, therefore, the image processing unit 38 performs image processing for emphasizing the contrast on the breast image G0 in a case where the breast type is identified as the high density type. In this manner, in a case where the breast type is identified as the high density type, it is possible to emphasize the contrast of the breast image G0 by performing image processing for emphasizing the contrast on the breast image. As described above, oversight of the lesion can be reduced by using the breast image G0 in which the contrast is emphasized.

On the other hand, in a case where the identified breast type is a fat type, the image processing unit 38 may increase the density (that is, make the breast image dark). As a result, it is possible to obtain the breast image G0 having a fat-like image density.

In each of the embodiments described above, the equation for calculating the average mammary gland dose, which is the average value of the dose absorbed in the mammary gland for the entire mammary gland, may be changed according to the identified breast type. Here, the average mammary gland dose is calculated by multiplying the radiation dose by an absorbed dose conversion coefficient. For example, in a case where the breast type is identified as a high density type, the average mammary gland dose may be calculated by increasing the value of the absorbed dose conversion coefficient or the like.

In each of the embodiments described above, imaging conditions at the time of next imaging may be changed according to the identified breast type. Here, as imaging conditions to be changed, at least one of the tube voltage or the mAs value can be used. For example, in a case where the breast type is identified as a type other than the high density type, it is possible to reduce the exposure dose to the breast M while maintaining the image quality of the breast image by reducing at least one of the tube voltage or the mAs value.

In each of the embodiments described above, the arm unit 12 of the radiographic image capturing apparatus 1 can be configured so that its end portion to which the irradiation unit 14 is attached can rotate. By rotating the arm unit 12 in this manner, the radiographic image capturing apparatus 1 can acquire a tomographic image of the breast M by performing tomosynthesis imaging. The tomosynthesis imaging is a method in which, in order to observe an affected part in more detail, an X-ray source is moved to irradiate a subject with radiation from a plurality of radiation source positions to perform imaging and a tomographic image emphasizing a desired tomographic plane is generated from a plurality of projection images acquired as described above. In tomosynthesis imaging, a plurality of projection images are acquired by imaging the subject at a plurality of radiation source positions by moving the X-ray source in parallel with a radiation detector or so as to draw a circular or elliptical arc according to the characteristics of the imaging apparatus or required tomographic images and the projection images are reconstructed using a reconstruction method, such as a shift addition method, a simple back projection method, or a filtered back projection method (FBP method), to generate a tomographic image.

As described above, in a case where the radiographic image capturing apparatus 1 is configured so as to be able to perform tomosynthesis imaging, whether or not to perform tomosynthesis imaging subsequent to the imaging of the breast M may be controlled according to the identified breast type in each of the embodiments described above. For example, in a case where the identified breast type is a high density type, it is difficult to detect a lesion based on the breast image G0. Therefore, in a case where the identified breast type is a high density type, the radiographic image capturing apparatus 1 may be controlled so as to perform tomosynthesis imaging subsequent to the imaging of the breast M.

In each of the embodiments described above, the second index value is acquired based on the strength of the boundary and the distance from the skin line. However, the second index value may be acquired based on one of the strength of the boundary and the distance from the skin line.

In each of the embodiments described above, the second detection unit 34 detects the boundary between the adipose tissue and the mammary gland tissue in the breast region A1 based on the difference value between the line profiles. However, the invention is not limited thereto. For example, it is possible to detect the boundary between the adipose tissue and the mammary gland tissue in the breast region A1 using any method, such as a method using a differential filter.

What is claimed is:

1. A breast type identification device, executed by a plurality of integrated circuits comprising:
    a first detection unit to detect a breast region and a skin line from a breast image obtained by imaging a breast with radiation;
    a first index value acquisition unit to acquire a first index value indicating a single composition degree of the breast region;
    a second detection unit to detect a boundary between an adipose tissue and a mammary gland tissue in a predetermined range and generate a line profile at a plurality of positions from the skin line toward an inside of the breast region in the breast image;
    a second index value acquisition unit to acquire a second index value indicating a degree of clogging of mammary glands with respect to the breast region based on at least one of a strength of the boundary or a distance from the skin line in each of the plurality of the line profiles; and
    an identification unit to identify a type of the breast based on the first and second index values.

2. The breast type identification device according to claim 1,
    wherein the first index value acquisition unit acquires is configured to acquire the first index value based on a histogram in the breast region.

3. The breast type identification device according to claim 1,
    wherein the second detection unit detects a position where a signal value changes with a peak in the line profile as the boundary.

4. The breast type identification device according to claim 1, further comprising:
    a display controller that displays the type of the breast on a display unit.

5. The breast type identification device according to claim 4,
    wherein the display controller further performs warning display according to the type of the breast.

6. A breast type identification method, comprising using one or more processors for:
    detecting a breast region and a skin line from a breast image obtained by imaging a breast with radiation;
    acquiring a first index value indicating a single composition degree of the breast region;
    detecting a boundary between an adipose tissue and a mammary gland tissue in a predetermined range and generates a line profile at a plurality of positions from the skin line toward an inside of the breast region in the breast image;
    acquiring a second index value indicating a degree of clogging of mammary glands with respect to the breast region based on at least one of a strength of the boundary or a distance from the skin line in each of the plurality of the line profiles; and
    identifying a type of the breast based on the first and second index values.

7. A non-transitory computer-readable storage medium that stores a breast type identification program causing a computer to execute:
    detecting a breast region and a skin line from a breast image obtained by imaging a breast with radiation;
    acquiring a first index value indicating a single composition degree of the breast region;
    detecting a boundary between an adipose tissue and a mammary gland tissue in a predetermined range and generating a line profile at a plurality of positions from the skin line toward an inside of the breast region in the breast image;
    acquiring a second index value indicating a degree of clogging of mammary glands with respect to the breast region based on at least one of a strength of the boundary or a distance from the skin line in each of the plurality of the line profiles; and
    identifying a type of the breast based on the first and second index values.

8. The breast type identification device according to claim 3,
    wherein the second index value acquisition unit acquires the second index value by multiplying an index value indicating the strength of the boundary by a weight coefficient based on the distance from the skin line in each of the plurality of the line profiles and adding an index value indicating the strength of the boundary after being multiplied by the weighting coefficient for each of the plurality of the line profiles.

* * * * *